United States Patent [19]
Kirschner et al.

[11] Patent Number: 5,942,218
[45] Date of Patent: Aug. 24, 1999

[54] ANTI-INFECTIVE MATERIAL

[75] Inventors: Ulrich Kirschner; Frank Jethon, both of Bad Homburg; Frank Rauch, München, all of Germany

[73] Assignee: Fresenius AG, Bad Homburg, Germany

[21] Appl. No.: 08/955,132

[22] Filed: Oct. 21, 1997

Related U.S. Application Data

[63] Continuation-in-part of application No. 08/553,305, filed as application No. PCT/EP94/01587, May 17, 1994.

[30] Foreign Application Priority Data

May 26, 1993 [DE] Germany ................................ 43 17 477

[51] Int. Cl.$^6$ ................ A61K 31/74; A61K 31/155; A01N 37/52
[52] U.S. Cl. ...................... 424/78.08; 424/78.07; 514/635
[58] Field of Search .................. 424/78.07, 78.08; 514/635

[56] References Cited

U.S. PATENT DOCUMENTS

| | | | |
|---|---|---|---|
| 4,654,208 | 3/1987 | Stockel et al. | 424/78 |
| 4,758,595 | 7/1988 | Ogunbiyi et al. | 514/635 |
| 4,891,423 | 1/1990 | Stockel | 528/422 |
| 5,183,664 | 2/1993 | Ansell | 424/445 |

FOREIGN PATENT DOCUMENTS

| | | |
|---|---|---|
| 0 450 117 | 2/1990 | European Pat. Off. |
| WO 86/02001 | 4/1986 | WIPO |

OTHER PUBLICATIONS

Gilbert et al., "Synergism within polyhexamethylene biguanide biocide formulations", Journal of Applied Bacteriology, 69, 593–598, 1990.

*Primary Examiner*—Jose' G. Dees
*Assistant Examiner*—Marina Lamm
*Attorney, Agent, or Firm*—Omri M. Behr, Esq.

[57] ABSTRACT

The subject matter comprises anti-infective materials such as antimicrobial materials based upon poly(hexamethylene) biguanide having a weight proportion of said polymer containing 5 or less units per chain is less than 2% based on entire polymer weight, which are suitably in the form of a wound antiseptic and/or a wound treating material or a material for anti-microbial, antiviral, and/or antiparasitic treatment which may suitably be administered by the intravenous mode. The utilization concentration of the poly (hexamethylene)biguanide as a wound antiseptic and/or a wound treatment material suitably lies in the range of 0.001 through 0.05 wt. %, in particular 0.005 through 0.012 wt. %. As compared to the known disinfective materials based upon poly(hexamethylene)biguanide which have been utilized as wound antiseptics and wound treatment materials, the poly-(hexamethylene)biguanides utilized in the present invention have a higher mean molecular weight and demonstrate an increased microbicidal activity coupled with lower toxicity and are free of side effects on the central nervous system.

6 Claims, 2 Drawing Sheets

ANTI-INFECTIVE MATERIAL

RELATED APPLICATIONS

This application is a continuation-in-part of application Ser. No. 08/553,305, filed Mar. 8, 1996, now abandoned, which was the National Stage of International Application No. PCT/EP94/01587, filed May 17, 1994.

FIELD OF THE INVENTION

The present invention is directed to an anti-infective material based upon poly(hexamethylene)biguanide, in particular in the form of a wound antiseptic and/or a wound treatment material and/or a solution for intravenous administration, as well as the use of poly(hexamethylene) biguanide for the production of an anti-infective material such as a disinfecting material, a wound antiseptic and/or a wound treatment material, as well as an antimicrobial, anti-viral, and/or antiparasitic material, preferably for intravenous administration.

STATE OF THE ART

It is known from the state of the art that poly (hexamethylene) biguanide (PHMB) has bacteriocidal and fungicidal action (see, for example, British Patent 12 02 495). PHMB is thus used in many areas as a disinfectant material, for example in the form of solutions or sprays. Uses are found, for example, in the food industry for the cleaning and disinfection of rooms and equipment, for the stabilization of drinks and for the cleaning and stabilization of water, for example also in swimming pools for the combatting of algal and bacterial growth. From German published application DE-OS 35 37 627, it is known that by the combination of PHMB having mean molecular weight of from 1700 through 1500 with a small amount of polyethylene glycol, disinfectant agents are obtained which can also be used as local antiseptics in wound treatment. In accordance with this patent application, PHMB may be suitably used as, for example, its hydrochloride which is sold under the trademark Vantocil® IB by ICI.

In EP 04 50 117, there is described a Ringer solution and its use as a local wound treating medicament having bacteriocidal action, wherein the lactate-free Ringer solution additionally comprises a 0.1 % to 0.2% solution of a concentrate dissolved therein comprising 20% aqueous poly (hexamethylene)biguanide-hydrochloride in which, for each 100 ml., 1 gram of polyethylene glycol having a molecular weight of about 4,000 is dissolved. As a suitable form of PHMB there is similarly described the material sold under the trademark Vantocil® IB by ICI. Under the trademark Lavasept®, a product is known for wound healing wherein the Lavasept® concentrate comprises an aqueous solution of 20 wt. % of PHMB and 1 wt. % of polyethylene glycol 4,000, wherein the PHMB is the commercial product Vantocil® IB sold by ICI.

In U.S. Pat. No. 4,758,595 (1) solutions are described which contain a microbicidal or fungicidally effective amount of a biguanide or an aqueously soluble salt thereof in amounts ranging from 0.000001 through 0.0003 wt. % which may be utilized for contact lenses, ophthalmic products and dermatological formulations which are utilized in the vicinity of the eye.

From British Patent 1 432 345 (2) combinations are known for use in relation to eyes and contact lenses which contain at least an ophthalmically acceptable polymeric biguanide.

SUMMARY OF THE INVENTION

The task of the present invention is to provide an anti-infective material, which may be used, in particular, a wound antiseptic and/or a wound treatment material both for prophylaxis and treatment of infections such as an antimicrobial, antiviral, and/or anti-parasitic material which is more effective than the known disinfectant materials, for example anti-microbial materials and which at the same time possesses a lower toxicity.

It should be understood that in this art, the polymers do not have a specific molecular wright but rather a more or less "bell curve" distribution. The mean molecular weight as used herein is the value at the top of the distribution curve.

In accordance with the present invention, it has surprisingly been found that poly(hexamethylene)biguanide which has a mean molecular weight which is higher than the molecular weight of the poly(hexa-methylene)-biguanide as disclosed in DE OS 35 37 627 and EP 04 50 117 which represents the state of the art, and in particular a poly (hexamethylene)-biguanide, as is disclosed in the state of the art in DE-OS 35 37 627 and EP 0 450 117, from which however the lower molecular weight portions have been removed, demonstrate an improved microbicidal activity with respect to the previously utilized poly(hexamethylene) biguanide which activity is similarly to be observed with respect not only to bacteria but to fungi and viruses as well.

PHMB has the following formula:

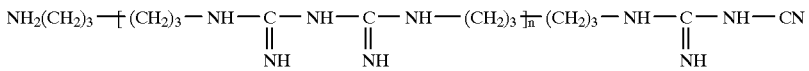

n means the level polymerization of the PHMB.

In the present invention, there is provided—compared to the previously utilized PHMB—a PHMB with higher mean molecular weight which has been freed from most of the low molecular weight PHMB portions and which exhibits a lower toxicity at the same level of activity. Further it has been surprisingly found that the serious central nervous system disturbances which have been observed with respect to the previously utilized PHMB do not occur with PHMB of higher mean molecular weight.

In accordance with the present invention, it has been surprisingly found that this—free of central nervous system side effects—enhanced activity and lower toxicity can be obtained utilizing poly(hexamethylene)-biguanide with a mean molecular weight in the region of 2,900 through 15,000. Particularly preferred is a poly(hexamethylene) biguanide with a mean molecular weight in the region of 3,000 to 8,000 and in particular a PHMB having a mean molecular weight in the region of 3,200 to 5,000, for example a PHMB with a mean molecular weight of between 3,500 and 4,500. The molecular weight determination is carried out by viscosimetric methods. The PHMB utilized in accordance with the present invention with the mentioned mean molecular weight is a water soluble material having minimal toxicity which has been substantially freed from the toxic lower molecular weight portions of PHMB, that is to say the synthetic precursors or its derivatives.

It will be understood that the term "mean" is the summation of fractions of molecular weights which are both higher and lower, i.e., n has various values. In order to achieve the product having the desirable characteristics of low loxicity, conventional PHMB such as PHMB having a mean molecular weight of about 2610 is subjected to fractional filtration wherein the lower molecular weight fractions are removed. The resulting fraction filtered PHMB contains fractions where the oligomers having a value of n=5 or less, constitute less than 2 wt %, preferably less than 0.5 wt %, most preferably less 0.1 wt %.

The formation of the poly(hexamethylene)biguanides of the present invention occurs thereby that poly(hexamethylene)biguanide is produced by the known methods, for example such as those disclosed in DE-PS 16 20 938 or GB-PS 12 02 495, whose disclosure is entirely incorporated herein by reference and which is separated, by known means, from the undesired molecular weight section of the thus obtained PHMB, for example by dialysis, molecular filtration, HPLC, gel permeation chromatography, fractionating precipitation and the like.

The preparation may also carried out in that the unwanted toxic lower molecular weight fractions may be separated in the previously described manner from commercially available PHMB for example from Vantocil® IB or Arlagard®E.

The PHMB utilized in accordance with the present invention may exist either in free form or in the form of a water soluble salt, for example as hydrochloride, as a powder (for example freeze dried) in 100% concentration or in aqueous solution. It may utilized in concentrations up to 40 wt. % for example from 2–40 wt. %, suitably 3–30 wt. %, in particular 4–20 wt. %, for example 4 wt. %, 4.5 wt. %, 5 wt. %, 6 wt. %, or 20 wt. % in aqueous solution (that is to say as a concentrate).

Under the term "PHMB" one should include both poly(hexamethylene)biguanide per se as well as the poly(hexamethylene)-biguanide in the form of an aqueous solution.

The concentration in which the PHMB is utilized in the present invention suitably the aqueous solution of PHMB in the anti-infective medium of the present invention, for example antimicrobial substances, depends upon the desired purpose of use of the anti-infective material of the present invention. Suitable concentrations, generally speaking, lie in the range of between 0.001 through 0.05 wt. %, suitably in the range of 0.004 through 0.03 wt. %, in particular in the region of 0.005 through 0.012 wt. %, suitably 0.005 wt. %, 0.006 wt. % or 0.012 wt. %.

The anti-infective materials of the present invention may contain surface tension reducing tensides such as for example polyethylene glycol. Suitably there is utilized polyethylene glycol having a molecular weight of from 1,500 through 6,000 and in particular such a polyethylene glycol having a molecular weight of 4,000, such as is sold under the trademark Lutrol® E4,000 by BASF AG. The relationship of PHMB to the tenside suitably lies in the range of 6:1 through 24:1, suitably in the range of 12:1 through 22:1 and is particularly desirable at 20:1.

The anti-infective materials may be utilized, for example, as disinfecting materials, for prophylaxis and/or treatment of infections, as antimicrobial materials, as antiviral materials, as antiparasitic materials, as wound antiseptics and/or as wound treatment materials and are particularly preferred as wound antiseptics and/or wound treatment materials and for antimicrobial, antiviral, and/or antiparasitic treatment. They can be utilized in different ways, for example locally or systemically, orally, rectally, vaginally, or intravenously, preferably intravenously. They may be used with humans and animals, preferably with humans. The preferred utilization for antimicrobial, antiviral and/or antiparasitic treatment is through intravenous administration, in particular for antimicrobial treatment through intravenous administration.

Depending on the desired treatment, the materials of the present invention can be provided in a variety of utilization forms, in particular pharmaceutical preparations such as, for example, in the form of aqueous solutions (for example as a component in a lactate-free Ringer solution or saline solution suitably in a lactate-free Ringer solution), emulsions, suspensions, gels, ointments, creams, tablets, capsules, dragees, suppositories and the like. In these forms of preparation there may be additionally utilized, for the formation of the particular preparation form, necessary conventional auxiliary and supplemental materials.

In addition to the improved effectiveness relative to materials based on PHMB having a lower molecular weight, the materials of the present invention have a better tolerance and tissue compatibility, show no resistance formation and do not give rise to central nervous system disturbances, paralytic symptoms, and other systemic side effects and are less toxic than the disinfectant material disclosed in DE-OS 35 37 627 based on PHMB having a molecular weight of between 1,700 to 2,500 as well as the commercial product Lavasept® (PHMB mean molecular weight 2,610). While the previously utilized commercial product Lavasept® containing PHMB (polyhexanidium) with mean molecular weight of 2,610 gives rise to 10% hemolysis at a blood level of merely 0.21%, the use of PHMB having a mean molecular weight of 4,000 gives rise to 10% hemolysis only at a blood level of 0.5%.

For use as a wound antiseptic and/or wound treatment material the poly(hexamethylene)biguanide utilized in the present invention suitably the previously mentioned aqueous concentrated solution of PHMB is diluted with water, lactate-free Ringer solution or saline solution, suitably with lactate-free Ringer solution. For such a utilization the suitable concentration of PHMB in water, lactate-free Ringer solution or saline solution, generally speaking lies in the region of from 0.001 through 0.05 wt. %, suitably in the region of 0.004 to 0.03 wt. %, in particular in the region of 0.05 through 0.012 wt. %, for example at 0.005 wt. %, 0.06 wt. % or 0.012 wt. %. In this concentration the materials of the present invention show excellent microbiostatic as well as microbial activity against all clinically relevant organisms such as Staphylococci, Coli, Pseudomonas, Proteus, Aerobacter and Anaerobacter, fungi, viruses, amoeba, protozoa, such as for example Leishmamniae and other parasites which are substantially unreduced even in the presence of albumin.

The saline solution can be utilized at a concentration of 0.4 through 1.2 wt. %, suitably however the physiological, that is to say 0.9 wt. % saline is used.

Based upon the foregoing surprising properties of the material of the present invention, these materials may be utilized for all those purposes where the previously known poly(hexamethylene)biguanide containing disinfection materials have been utilized, whereby in order to obtain comparably desired results on the basis of the properties of the PHMB utilized in accordance with the present invention, the anti-infective, antimicrobial materials may be used in substantially lower concentrations than for the known disinfecting material. Additionally thereto with respect to the wound antiseptic and wound handling materials of the present invention, there is a better tissue tolerance and a substantial lower toxicity. The PHMB utilized in accordance with the present invention is resorbed in much lower amounts than those poly(hexamethylene)biguanides previously utilized for this purpose. Furthermore, during prolonged usage of the solutions in accordance with the present invention, no change in the good tissue tolerance to be observed. Even during longer treatments, no appearance of local irritation is noted either in the wounds or on the skin. The materials of the present invention may therefore be used as local antiseptics and for the wound treatment, for example for wound healing in many areas of medical practice. Thus the solutions of the present invention may be utilized in the case of different surgical infections, for example with chronic bone infections, post-operative infection sources following osteosynthesis, with soft tissue infections, for example with respect to operation wounds after appendectomy or abdominal intrusions, skin, subcutaneous and deeper soft tissue abscesses or hand and finger infections, in peritonitis and infection imperilled abdominal intrusions as well as different infections in dental surgery, for example after removal of infected teeth and cysts, dentitio difficilis, infected gum pockets or alveolus, osteomyelitis of the jaw bone and dentogenic maxillary sinusitis, as well as prophylactic use as a wound rinsing means for the operational area. The use of a material of the present invention can be in the form of washes of focal inflammations in preparation for the clearance of focal inflammations, wound washes, as preoperative washes or washes during an operation, in the form of tampons saturated with a solution in accordance with the present invention (for example dental surgery) or plaster bandages (for recovering post-operatively open-remaining wounds) and the like.

In therapeutic use, an intermittent application is preferred, wherein the infected wound is soaked 1 to 3 times daily, corresponding to the therapeutic needs, with the material of the present invention or is washed out with it. Furthermore, the material of the present invention may also be used in wash/suction drainage for internal washes. For intraoperative prophylaxis, the material of the present invention may utilized during the entire duration of the operation for washing the operative area as well as the scouring of implants with compresses wherein amounts from to 1 to 2 l. may be readily applied.

The solution of the present invention may also be utilized with contact lenses, for example for the storing of contact lenses, as wash solutions for contact lenses and for the washing of eyes.

For the prophylaxis and treatment of infections, for example for the antimicrobial treatment of humans and animals through intravenous administration, the PHMB utilized in the present invention suitably in the aforementioned concentrated aqueous solution of the PHMB utilized in the present invention, is diluted with water, saline, or lactate-free Ringer solution, suitably lactate-free Ringer solution. Suitable concentrations of the PHMB of the present invention in water, saline, or lactate-free Ringer solution for this use lie in the general range of 0.000001 to 0.05 wt. %, suitably in the range of 0.0001 to 0.3 wt. %, in particular in the range of 0.001 to 0.1 wt. % and may for example be, 0.00005 wt. %, 0.0005 wt. %, 0.005 wt. %, 0.0012 wt. %, or 0.01 wt. %. In this concentration the intravenously administered solutions in accordance with the present invention demonstrate an excellent microbiostatic, suitably microbicidal action against all clinically relevant organisms such as Staphylococci, Coli, Pseudomonas, Proteus, Aerobes and Anaerobes, fungi, viruses, amoeba, protozoa, such as for example Leishmannai and other parasites which even in the presence of albumin are substantially not reduced.

For the intravenous administration there may also be utilized the previously mentioned solutions which contain surface tension reducing tensides. However, they are preferably free of such tensides. In these solutions there may furthermore, as stated, the additionally added conventional electrolytes such as the conventional auxiliary and supplemental materials. These intravenously administrable solutions are suitable for the prophylaxis and/or treatment of infections generated by clinically important organisms such as Staphylococci, Coli, Pseudomonas, Proteus, Anaerobes, fungi, and viruses. They are particularly suitable for the prophylaxis and treatment of microbial infections caused by Anaerobes, fungi, viruses, protozoa and other parasites. In experiments it has been the surprising finding that the appearances of paralysis such central nervous system disturbances which occur during the use of Lavasept® solutions or solutions which contain PHMB in the middle molecular weight range of 2,610 which also contain the lower molecular weight portions of PHMB as part thereof are not observed. The solutions of the present invention are therefore only minimally toxic and demonstrate a higher effectiveness and are furthermore surprisingly better tolerated than the previously described known solutions based on PHMB having a mean molecular weight of from 1,700 to 2,600.

The solutions to be administered intravenously can suitably be utilized at a dosage level of between 0.01 to 20 ml/kg body weight, suitably in doses of 0.1 ml/kg body weight or 10 ml/kg body weight.

MODES OF CARRYING OUT THE INVENTION

The following examples serve to illustrate the present invention.

EXAMPLE 1

Figure 1:
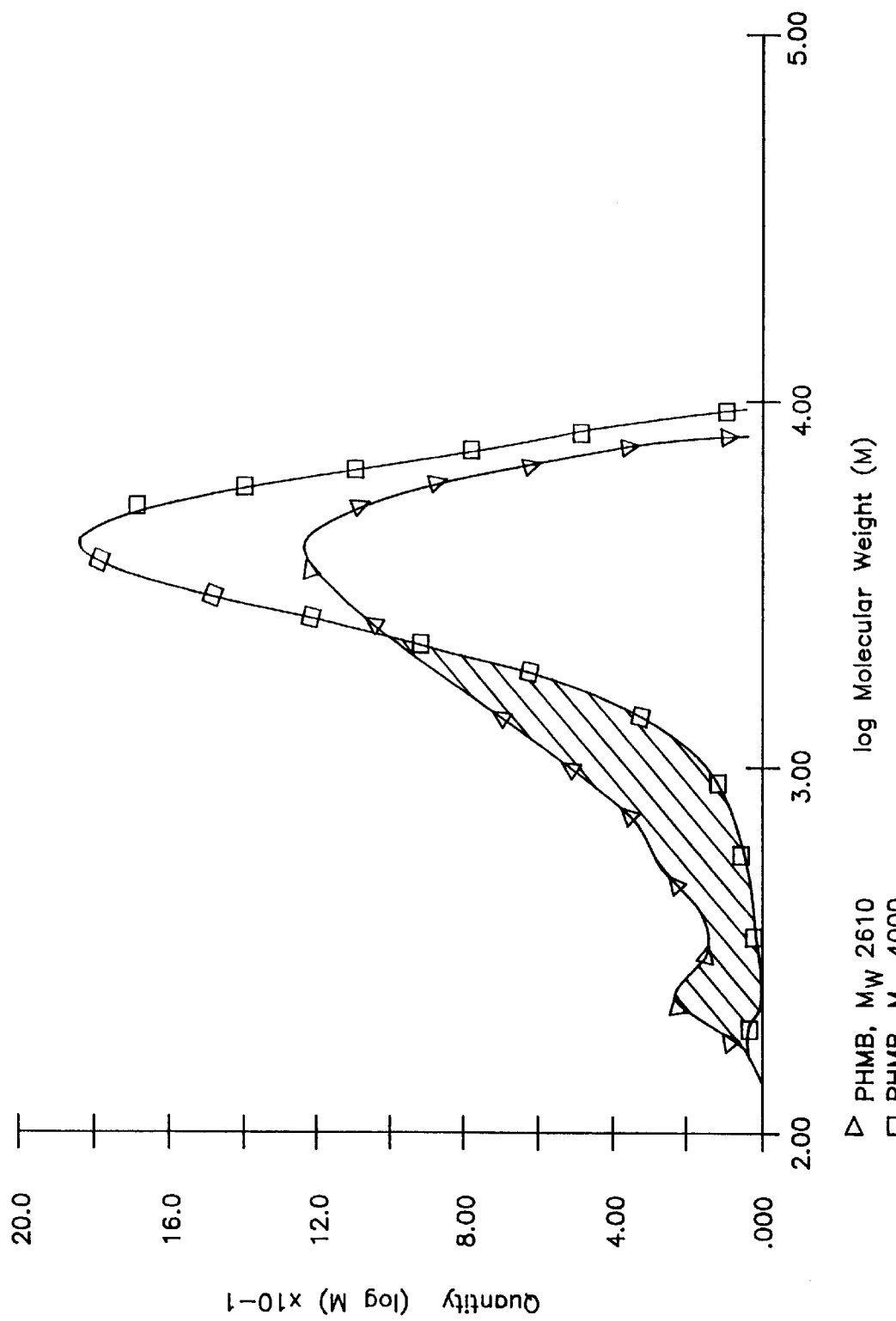
FIG. 1 shows the molecular weight distribution of PHMB of mean molecular weight 4,000 in accordance with the present invention and commercially available PHMB having a mean molecular weight of 2,600.

Commercially available PHMB 2610 is subjected to fractional filtration which removes approximately 75% of the initial polymer mixture. This results in a shift of the mean molecular weight fraction in the manner illustrated in FIG. 1 from approximately 2610 to approximately 4,000. An analysis of the molecular weight and quantity distribution, as illustrated in FIG. 1, may be set forth in the following table which can be deduced from the information on FIG. 1.

| Polymer | Polymer Distribution in a 100% PHMB Lyophilisate before Fractional Filtration (Initial $M_w$ 2610) (Relative Weight of Fractions of a Given Polymerization #) | Polymer Distribution in a 100% PHMB Lyophilisate after Fractional Filtration (Initial $M_w$ 2610) (Relative Weight of Fractions of a Given Polymerization #) |
|---|---|---|
| n = 1 | $>10^1$ | $<10^{-1}$ |
| n = 2 | $>10^1$ | $<10^0$ |
| n = 3 | $>10^2$ | $<10^0$ |
| n = 4 | $>10^3$ | $<10^1$ |
| n = 5 | $>10^7$ | $<10^3$ |
| n = 18 | $<10^{12}$ | $>10^{17}$ |

The analysis of molecular weight fractions is carried out by gel permeation chromatography. A 4–5 mg sample was dissolved in a suitable solvent and the solution injected into a gel permeation chromatography column. The detector utilized was a differential viscosimeter (Model 110, manufactured by Viscotek), as well as a Shodex Differential Refractometer (SE-71) as well as a measuring device manufactured by Viscotek.

The methodology utilized was published in German in GIT Fachzeitschrift fur Labor, 4/1990, pages 467–477 and GIT Fachzeitschrift Labor 5/1990, pages 656–662. The determination of mean molecular weight of the sample resulted from the calibration used in dextran standards by means of the strip method which is also disclosed in the foregoing article.

Thus, a review of the foregoing the foregoing table shows that in the samples subjected to fractional filtration, the amount of polymer where n=18, exceeds the amount of polymer where n=1, by a factor of $10^{18}$, i.e., $(10^{17+1})$. Similarly, in the sample prior to fractional filtration, this ratio is only $10^{11}$, i.e., $(10^{12-1})$. This can further be interpreted by showing that the amount of high fraction PHMB, i.e., n=18 between the prefiltration and the postfiltration, is a factor of $10^7$. i.e., $10^{18-11}$. These factors, when integrated, give rise to an increase of means molecular weight from 2610 to 4000.

From the foregoing table, it may be seen that the proportion of a polymer, wherein n=18 ($M_w$ circa 4,000), after fractional filtration exceeds the amount of polymer wherein n=5 (i.e., $M_w$ about 1100) by a factor of $10^{14}$, whereas prior to fractionation, the mixture comprised a ratio of n=18 to n=5 of only $10^5$.

In this particular example therefore, the polymer fraction of n=5 or less constitutes less than 0.1 wt %, based upon the entire weight of polymer mixture.

Utilizing poly(hexamethylene)biguanide having a mean molecular weight $M_w$ of 3,500, polyethylene glycol 4,000 (Lutro® E 4000, BASF AG) and water, there is produced a mixture of the present invention having the following composition:

| | |
|---|---|
| Poly(hexamethylene)biguanide-Hydrochloride, $M_w$ 3,500 | 6 wt. % |
| Polyethylene glycol, $M_w$ 4,000 | 0.3 wt. % |
| Water | 93.7 wt. % |

The poly(hexamethylene)biguanide-hydrochloride utilized herein is separated in the known manner by the fractional filtration of the commercially available poly(hexamethylene)biguanide product- Vantocil®IB or Arlagard E of ICI. Vantocil® IB or suitably Arlagard E is an aqueous solution which contains 20% of poly(hexamethylene)biguanide hydrochloride as the active material.

EXAMPLE 2

The production of the solution of the present invention is carried out in accordance with Example 1 except that in place of PHMB hydrochloride, the corresponding PHMB is utilized.

EXAMPLE 3

For the formation of wound antiseptic and wound handling material, a 0.2% solution produced in accordance with Example 1 and 2 are diluted with lactate-free Ringer solution to yield a final concentration of PHMB ($M_w$ 3,500) of 0.012 wt. %.

EXAMPLE 4

From PHMB having a mean molecular weight of 3,500, polyethylene glycol 4,000 and water, in the same manner as described in Example 1 by mixing the components, a solution of the present invention the following composition was formed:

| | |
|---|---|
| Poly(hexamethylene)biguanide-Hydrochloride, $M_w$ 3,500 | 20 wt. % |
| Polyethylene glycol, $M_w$ 4,000 | 1.0 wt. % |
| Water | 79 wt. % |

As PHMB and polyethylene glycol, the products already utilized in Example 1 were employed.

EXAMPLE 5

From PHMB hydrochloride and polyethylene glycol as described in Examples 1 and 4, together with water by mixture thereof, as described in Example 1, a solution of the present invention of the following composition was produced:

| | |
|---|---|
| Poly(hexamethylene)biguanide-Hydrochloride, $M_w$ 3,500 | 5 wt. % |
| Polyethylene glycol, $M_w$ 4,000 | 0.3 wt. % |
| Water | 94.7 wt. % |

EXAMPLE 6

For the formation of a further solution in accordance with the present invention, Example 1 was repeated except that in place of the utilized PHMB hydrochloride, $M_w$ 3,500, PHMB with a mean molecular weight $M_w$ 4,000 as already described in Example 1 was utilized. From FIG. 1, the mean molecular weight distribution of PHMB 4,000 in comparison with that of the commercially available PHMB 2,600 may be noted.

EXAMPLE 7

For the formation of a further solution in accordance with the present invention, Example 4 is repeated except that in place of the there utilized PHMB hydrochloride mean molecular weight 3,500, there is utilized PHMB hydrochloride of mean molecular weight 5,000 produced in a similar manner.

EXAMPLE 8

In accordance with this example, the microbicidal effectiveness of PHMB produced in accordance with the present invention having a mean molecular weight of $M_w$ 3,500 is compared with the microbicidal effectiveness of Vantocil® IB. All experiments were carried out in accordance with the DGHM guideline 1/2.3 (quantitative suspension). The Ig-reduction factor (Rf) are obtained from the individual readings. In these tests inactivation is carried out utilizing 3% Tween 80+3% Saponin+0.1% Histidine+0.1% Cystine. Results of these investigations are set forth in the following Table 1 wherein there are the following meanings A Vantocil® IB, 20 wt. % PHMB, $M_w$ 2,610

B 5 wt. % solution of PHMB, $M_w$ 2,610

C 5 wt. % aqueous solution of PHMB, $M_w$ 3,500

The solutions were tested against certain test organisms in the designated concentration and tested during the indicated working times.

TABLE 1

| Concentration (%) | Rf "A" | Rf "B" | Rf "C" |
|---|---|---|---|
| a) Test organism: S. aureus: Reaction time: 2 minutes | | | |
| 0.2 | 2.0 | 1.0 | 2.0 |
| 0.1 | 1.1 | 0.95 | 1.1 |
| 0.05 | 1 | 0.85 | 1 |
| 0.01 | 0.95 | 0.8 | 0.9 |
| b) Test organism: S. aureus: Reaction time: 30 minutes | | | |
| 0.2 | >5 | >5 | >5 |
| 0.1 | >5 | >5 | >5 |
| 0.05 | 4.5 | 4.0 | 4.8 |
| 0.01 | 3.0 | 1.5 | 3.0 |
| c) Test organism: P. aeruginosa: Reaction time: 112 minute | | | |
| 0.2 | 0.3 | 0.0 | 0.3 |
| d) Test organism: P. aeruginosa: Reaction time: 2 minutes | | | |
| 0.2 | 1.5 | 0.2 | 1.5 |
| 0.1 | 1.4 | 0.0 | 1.4 |
| 0.01 | 0.2 | 0.0 | 0.2 |
| e) Test organism: S. aeruginosa: Reaction time: 30 minutes | | | |
| 0.2 | >5 | >5 | >5 |
| 0.1 | >5 | >5 | >5 |
| 0.05 | >5 | 2.8 | >5 |

EXAMPLE 9

Also for comparison purposes, however under particular loading, the following quantitative suspension tests were carried out in accordance with DGHM guideline 1/2.3. In the following Tables 2 and 3, there are summarized the results obtained in these tests together with the substrates added for loading and the test concentrations of the comparative test substances to be tested. The Ig-reduction factor are calculated from individual values and the tests were inactivated by 3% Tween 80+3% Saponin+0.1% Histidine+ 0.1% Cysteine.

TABLE 2

Test Organism: S. aureus
Loading: 1% Albumin
Test Concentration: 0.125 wt. % in Lactate-free Ringer solution
Test Substance A: Lavasept ® containing 20 wt. % PHMB, $M_w$ 2,610
Test Substance C: Solution in accordance with Example 4

| Reaction Time (min) | Rf "A" | Rf "B" | Ringer |
|---|---|---|---|
| 1 | 4.0 | >5 | 0 |
| 5 | 1.5 | 3.7 | 0 |
| 15 | 0 | 1.5 | 0 |

TABLE 3

Test Organism: S. aureus
Loading: 20% Blood
Test Concentration: 0.2 wt. % in Lactate-free Ringer solution
Test Substance A: Lavasept ® containing 20% PHMB, $M_w$ 2,610
Test Substance C: Solution in accordance with Example 5

| Time (min) | Rf "A" | Rf "C" |
|---|---|---|
| 2 | 1.2 | 1.2 |
| 15 | 2.0 | 2.1 |
| 30 | 2.2 | 2.2 |

EXAMPLE 10

In order to show the surprising superiority of the PHMB utilized in the present invention having a mean molecular weight $M_w$ of 3,500 over the PHMB having a mean molecular weight of 2,500, the PHMB utilized in accordance with the present invention having a molecular weight of 3,500 was compared with the bacteriocidal effectiveness and toxicity of PHMB having a mean molecular weight of 2,500. The test with respect to toxicity (hemolysis test) were carried out in the following manner:

It was determined whether during incubation with human blood with the test solutions, hemoglobin was released. The following solutions were tested in accordance with the methodology of H. Kreuzer, AMI-Reports I/81, page 14:

1 ml fresh citrate blood and 1 ml 1 % Saponin solution (dissolved in 0.9% saline);

1 ml fresh citrate blood and 1 ml 0.9% saline;

1 ml fresh citrate blood and 1 ml test solution;

1 ml fresh citrate blood and 1 ml Ringer solution.

The mixtures were incubated for 45 minutes at 37° C. and subsequently centrifuged for 5 minutes at 1,000 g. The hemoglobin test of the mixture with Saponin corresponds to 100% hemolysis and the hemoglobin content of the mixture was physiological saline acts as the null value.

In these experiments, it is found that the bacteriocidal activity rose by a factor of 3.3% when the molecular weight of the poly(hexamethylene)-biguanide rose from 2,500 to 3,500, while the concentration required for hemolysis rose by a factor of 2. The hemolysis was determined by the examination of the hemolytic activity of both poly (hexamethylene)biguanides having different molecular weights taking account of their bacteriocidal activity.

EXAMPLE 11

To prove the surprising superiority of the PHMB utilized in the present invention with respect to the previously utilized PHMB, a PHMB having a mean molecular weight $M_w$ of 4,000 was compared with a previously utilized PHMB having a molecular weight of 2,610 (see FIG. 1 as well as Example 6). The tests with respect to toxicity (hemolysis test) were carried out in the following manner:

It was determined whether during incubation with human blood with the test solutions that hemoglobin was released. The following solutions were tested in accordance with the methodology of H. Kreuzer, AMI-Reports 1/81, page 14:

1ml fresh citrate blood and 1 ml 1 % Saponin solution (dissolved in 0.9% saline);

1 ml fresh citrate blood and 1 ml 0.9% saline;

1 ml fresh citrate blood and 1 ml test solution;

1 ml fresh citrate blood and 1 ml Ringer solution.

Figure 2:
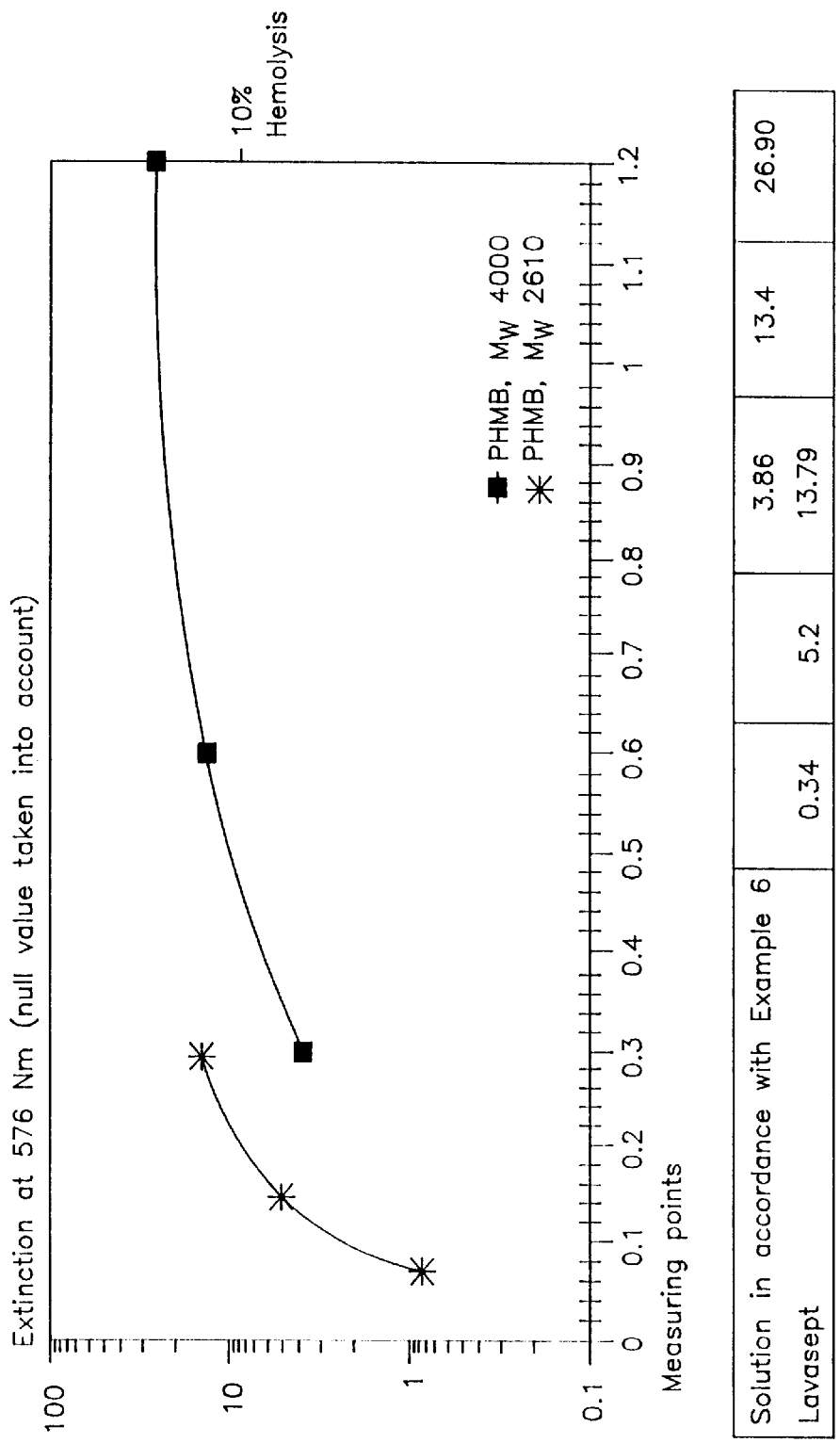
FIG. 2 shows the results of the hemodialysis.

The mixtures were incubated for 45 minutes at 37° C. and subsequently centrifuged for 5 minutes at 1,000 g. The hemoglobin test of the mixture with Saponin comprises 100% hemolysis and the hemoglobin content of the mixture was physiological saline acts as the null value. The results obtained in these researches may be seen in accompanying FIG. 2.

These results show that when utilizing the previously utilized PHMB for example Lavasept® having a mean molecular weight of 2,610, a 10% hemolysis already occurs at a level of 0.2% in blood whereas utilizing PHMB (solution in accordance with Example 6) having mean molecular weight $M_w$ 4,000, a 10% hemolysis only occurs utilizing 0.5% PHMB $M_w$ 4,000 in blood.

EXAMPLE 12

From PHMB at the mean molecular weight of 4,000 and water mixed together, a solution of the present invention having the following composition was formed:

PHMB, $M_w$ 4,000—4 wt. %
Water—96 wt. %
The PHMB utilized was obtained in accordance with the method described in Example 1.

EXAMPLE 13

From PHMB having a mean molecular weight 5,000 and water mixed together, a solution of the present invention having the following composition was obtained:
PHMB, $M_w$ 5,000—4.2 wt. %
Water—95.8 wt. %
The PHMB utilized was produced in accordance with the procedure of Example 1.

EXAMPLE 14

From PHMB of a mean molecular weight 4,500 and water and mixed together, a solution of the present invention having the following composition was obtained:
PHMB, $M_w$ 4,500—4.5 wt. %
Water—95.5 wt. %
The PHMB utilized was obtained by the method set forth in Example 1.

EXAMPLE 15

In order to provide a further solution in accordance with the present invention, Example 1 was repeated except that in place of the there utilized PHMB having a mean molecular of 3,500, there was utilized a mean molecular weight of 4,000 and the content thereof of polyethylene glycol ($M_w$ 4,000) was replaced by water.

EXAMPLE 16

The experiments set forth in Example 8 were repeated. However, as test solution "C" the solutions produced in accordance with Examples 12 through 15 were utilized. In these tests, the results obtained for the solutions of Examples 12 through 15 were comparable to those shown in Example 8.

EXAMPLE 17

From PHMB having a mean molecular weight of 4,000 and water mixed together, a solution of the present invention having the following composition was obtained:
PHMB, $M_w$ 4,000—20 wt. %
Water—80 wt. %
The PHMB utilized was produced in accordance with the method set forth in Example 1.

EXAMPLE 18

The suspension tests set forth in Example 9 were repeated but utilizing the following test substances:
Test Substance A: Lavasept containing 20% PHMB, $M_w$ 2,610
Test Substance C: Solution n accordance with Example 17
Test Substance D: Lavasept as in test sample A,. however without any polyethylene glycol content.
In these test results were obtained which are comparable to those set forth in Example 9.

EXAMPLE 19

For the formulation of a intravenously administrable solution for the prophylaxis and/or treatment of infections such as antimicrobial treatment, 0.2% of a solution produced in accordance with Example 15 are diluted with a lactate-free Ringer solution to yield a final concentration of PHMB, $M_w$ 4,000 of 0.0012 wt. %.

EXAMPLE 20

For the formation of a further intravenously administrable solution of the prophylaxis and/or treatment of infections such as antimicrobial treatment, 0.2% of a solution produced in accordance with Example 1 were diluted with lactate-free Ringer solution to a final concentration of PHMB, $M_w$ 4,000 of 0.01 wt. %.

EXAMPLE 21

For the formation of a further intravenously administrable solution 0.2% of the solution produced in accordance with Example 14 were diluted with 0.9% saline to yield a final concentration of PHMB, $M_w$ 4,500 of 0.005 wt. %.

EXAMPLE 22

For the formation of a further intravenously administrable solution 0.2% of the solution produced in accordance with Example 13 were diluted with 0.9% saline to yield a final concentration of PHMB, $M_w$ 5,000 of 0.00005 wt. %.

EXAMPLE 23

For the formation of a further intravenously administrable solution 0.2% of the solution produced in accordance with Example 12 were diluted with 0.9% saline to yield a final concentration of PHMB, $M_w$ 4,000 of 0.0005 wt. %.

EXAMPLE 24

For comparative purposes, the following solutions were examined as intravenous solutions with respect to the effectiveness as biocides.
Solution A: Lavasept® 0.2% in Ringer solution (concentration PHMB, $M_w$ 2,610:0.04%);
Solution B: Solution in accordance with Example 20 (concentration of PHMB, $M_w$, 4,000:0.01%).
The tests were carried out on Wistar Rats. The rats were slowly and continuously injected once into their tail vein with the solution under test. The rats were divided into three different groups, each containing 10 animals (each containing 5 male and 5 female animals) wherein there were administered to:
Group I: 5 ml/kg body weight of solution A;
Group II: 10 ml/kg body weight of solution A; and
Group III: 10 ml/kg body weight of solution B.
The test period was 14 days wherein observations were made after 10 minutes, 1 hour, 2 hours, 6 hours, and 24 hours after administration and thereafter daily to the end of the 14 day test period.
These tests show that while there was comparable weight gain in all of the groups, in Group I up to 2 hours after administration and in Group II up to 6 hours after administration a typical picture of paralytic symptoms (central nervous disturbances) were noted: sharply reduced activity, abdominal or hock position, abnormal gait, abnormal body posture, reduced body and abdominal tonality. In Group III no changes were noted. The typical picture of paralysis symptoms as noted in Groups I and II did not occur in Group III.

EXAMPLE 25

Preparation of a Gel

Utilizing the following components, a gel in accordance with the present invention was made in the conventional manner:

Lactate-free Ringer solution: 965.5 g
PHMB in accordance with Example 4:2.0 g
Hydroxyethyl cellulose (DAB) 32.5 g

EXAMPLE 26

For the formation of a further gel, Example 25 was repeated except that in place of the PHMB solution of Example 4, the PHMB solution of Example 17 was utilized.

EXAMPLE 27

Utilizing PHMB of a mean molecular weight of $M_w$ 6,000 and water a dilution of the present invention having the following composition was produced by mixing the same:

PHMB, $M_w$ 6,000 (sic): 4.2 wt. %
Water: 95.8 wt. %

The PHMB utilized was obtained in accordance with the procedure of Example 1.

EXAMPLE 28

For the formation of an intravenously administrable solution for the prophylaxis and/or treatment of infections such as antimicrobial treatment, 0.2% of the solution obtained in accordance with Example 27 was diluted lactate-free Ringer solution to yield an end concentration of PHMB, $M_w$ 6,000 to 0.0012 wt. %.

We claim:

1. An intravenously administrable anti-infection solution comprising poly(hexa-methylene)biguanide wherein the weight proportion of said polymer containing 5 or less units per chain is less than 2% based on entire polymer weight.

2. The solution of claim 1 wherein the poly(hexamethylene)biguanide has a concentration of between 0.000001 through 0.05 wt. %.

3. The solution of claim 2, wherein the concentration is between 0.0001 to 0.03 wt. %.

4. The solution of claim 3 having a concentration of between 0.001 to 0.01 wt. %.

5. A method of combatting infections comprising intravenously administering to a subject in need of same an anti-infective amount of poly(hexa-methylene)biguanide wherein the weight proportion of said polymer containing 5 or less units per chain is less than 2% based on entire polymer weight.

6. The composition of claim 5, wherein the proportion of polymer containing 5 units or less is less than 0.1%.

* * * * *